United States Patent
Lothstein et al.

(10) Patent No.: US 11,666,589 B2
(45) Date of Patent: Jun. 6, 2023

(54) PIVARUBICIN AND BENZARUBICIN COMPOSITIONS

(71) Applicant: Paradox Pharmaceuticals, Inc., Memphis, TN (US)

(72) Inventors: Leonard Lothstein, Eads, TN (US); Judith Soberman, Eads, TN (US); Tiffany N. Seagroves, Memphis, TN (US)

(*) Notice: Subject to any disclaimer, the term of this patent is extended or adjusted under 35 U.S.C. 154(b) by 0 days.

(21) Appl. No.: 17/190,317

(22) Filed: Mar. 2, 2021

(65) Prior Publication Data

US 2021/0268007 A1    Sep. 2, 2021

Related U.S. Application Data

(60) Provisional application No. 62/984,258, filed on Mar. 2, 2020.

(51) Int. Cl.
*A61K 31/704* (2006.01)
*A61K 47/14* (2017.01)
*A61P 35/00* (2006.01)
*A61K 47/02* (2006.01)
*A61K 47/10* (2017.01)

(52) U.S. Cl.
CPC ............ *A61K 31/704* (2013.01); *A61K 47/02* (2013.01); *A61K 47/10* (2013.01); *A61K 47/14* (2013.01); *A61P 35/00* (2018.01)

(58) Field of Classification Search
CPC ........ A61P 35/00; A61K 31/704; A61K 47/14
See application file for complete search history.

(56) References Cited

U.S. PATENT DOCUMENTS

| 4,610,977 A | * | 9/1986 | Israel | A61P 35/00 |
| | | | | 536/6.4 |
| 2006/0199775 A1 | * | 9/2006 | Lothstein | A61K 31/704 |
| | | | | 514/34 |

OTHER PUBLICATIONS

Pandey; Oncotarget, 2018, vol. 9 (No. 47), pp. 28514-28531.*
Pub Chem (https://pubchem.ncbi.nlm.nih.gov/compound/Polyoxyl-35-castor-oil#section=Deprecated-CAS; downloaded on Jun. 27, 2022).*

* cited by examiner

*Primary Examiner* — Pancham Bakshi
(74) *Attorney, Agent, or Firm* — Hylton-Rodic Law PLLC

(57) ABSTRACT

The present invention relates to compositions comprising at least one of pivarubicin and benzarubicin, or a pharmaceutically acceptable salt thereof, and methods for using the compositions in the treatment of triple negative breast cancer (TNBC) by administering an effective amount of the compositions to a subject. In some instances, the subject is a mammal, including at least one of human, feline, and canine mammals.

10 Claims, 9 Drawing Sheets

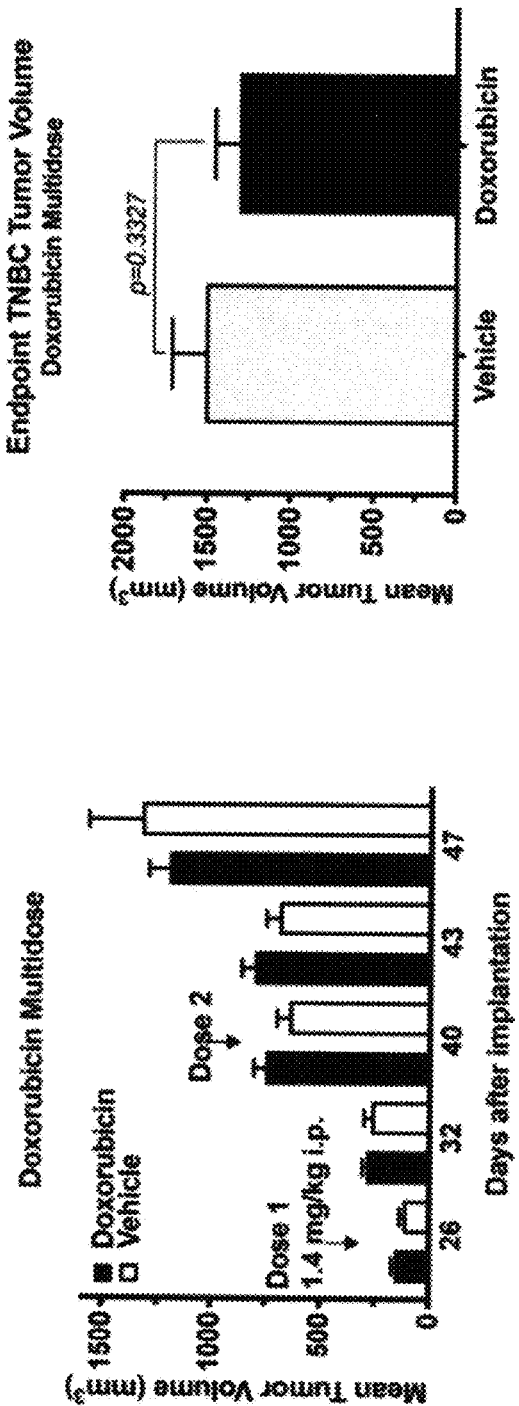
FIG. 7A
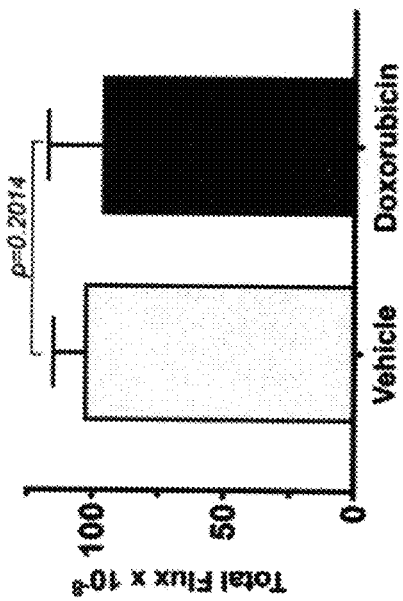
FIG. 7B
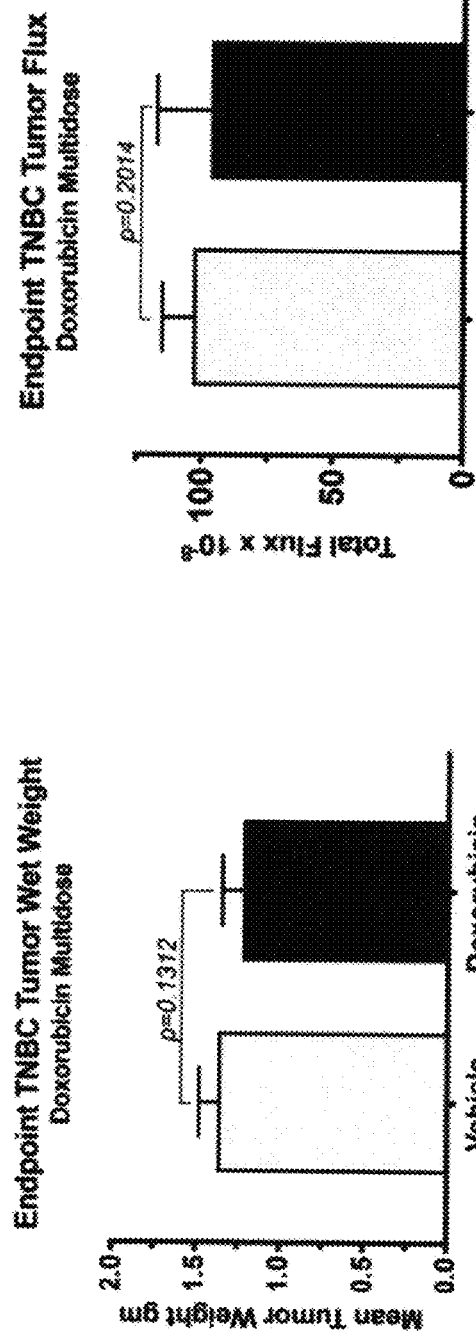
FIG. 7C
FIG. 7D

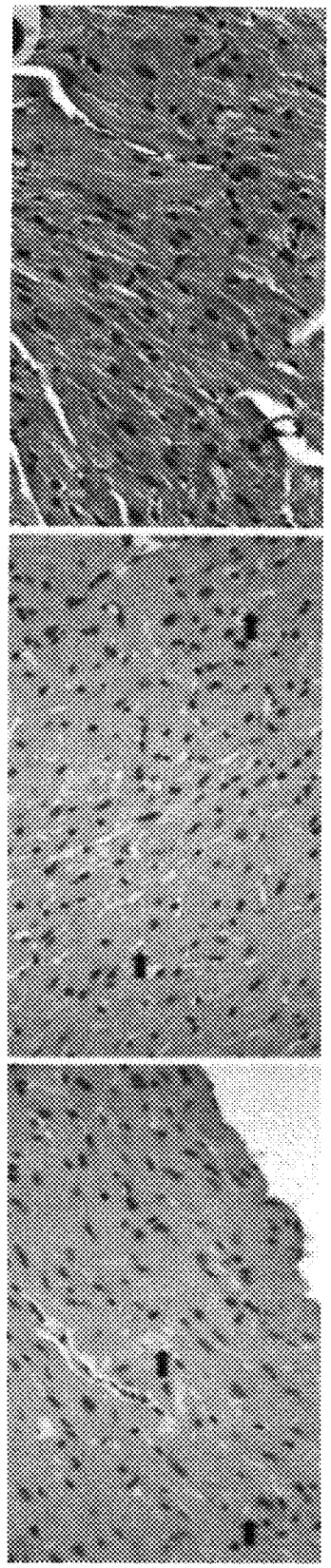

PIVARUBICIN AND BENZARUBICIN COMPOSITIONS

CROSS REFERENCE TO RELATED APPLICATIONS

This application claims the benefit of U.S. Provisional Application No. 62/984,258, filed on 2 Mar. 2020, entitled TREATMENT OF TRIPLE NEGATIVE BREAST CANCER. The entirety of the foregoing is hereby incorporated by reference.

STATEMENT OF FEDERALLY SPONSORED RESEARCH AND DEVELOPMENT

This invention was made with government support under NCI Grant No. R01CA138488 awarded by National Cancer Institute. The government has certain rights in the invention.

FIELD OF THE INVENTION

The field of the invention relates generally to method of treating cancer.

BACKGROUND

Triple-negative breast cancer (TNBC) is a highly aggressive subtype that neither expresses estrogen receptors (ER) and progesterone receptors nor overexpresses epidermal growth factor 2 receptor (HER2) and is unresponsive to anti-estrogen and anti-HER2 therapies. Consequently, current standard of care includes systemic cytotoxic drug combinations of anthracyclines, such as doxorubicin (DOX, "ADRIAMYCIN") or epirubicin, taxanes, cyclophosphamide and platinum compounds [1-3], with more targeted therapies undergoing clinical trials [4].

Despite initial sensitivity to chemotherapy, TNBC patients experience lower overall disease-free intervals compared with patients whose tumors express sex steroid hormone receptors [5], with an overall pCR of only 20-40% [6]. The limited cytotoxic efficacy of chemotherapy is likely due to multiple mechanisms of cellular drug resistance, as well as cell senescence and cytoprotective autophagy [1]. Further, the irreversible cardiotoxic effects of anthracyclines and, to a lesser extent, taxanes, cyclophosphamide and platinum compounds are well established and limit the cumulative doses of drugs that can be administered to achieve a curative outcome [7,8].

It is only very recently that triple-negative breast cancer (TNBC) was recognized as a unique sub-type of breast cancer. Perhaps the earliest mention of triple-negative breast cancer in the literature appears to be in a 2005 breast cancer genetic profiling article (Brenton J D, Carey L A, Ahmed A A, Caldas C. Molecular classification and molecular forecasting of breast cancer: J. Clin. Oncol. 2005; 23:7350-60). However, the precise genetic definition of TNBC was still being debated even as late as 2009.

There continues a need for novel TNBC chemotherapy different from that used to treat receptor-positive breast cancers has been discussed extensively in the literature (see, e.g., Anders, C. et al., The Evolution of Triple-Negative Breast Cancer: From Biology to Novel Therapeutics, ASCO Educational Book, 34-42 (2016)). In particular, a critical unmet need exists for safer and more effective treatments for TNBC that eliminate drug-resistant cell subpopulations without producing cardiotoxicities, thereby reducing the probability of recurrent disease and irreversible cardiac damage.

N-Benzyladriamycin-14-pivalate (also known as pivarubicin and AD 445) was designed and developed as a chemically stable congener of the experimental antitumor agent N-benzyladriamycin-14-valerate (also known as benzarubicin and AD 198) [9]. AD 198 has been previously shown to competitively bind to the C1b (diacylglycerol-binding) regulatory domain of conventional and novel isoforms of protein kinase C (PKC) in the cytoplasmic compartment of mammalian cells [10-12]. AD 198 is functionally distinct from DOX in its ability to trigger rapid, mitochondrial-dependent apoptosis through PKC-delta (PKCd) activation in a manner that circumvents multiple mechanisms of cellular drug resistance [12-16]. Further, through the specific activation of PKC-epsilon in mammalian cardiomyocytes, AD 198 confers cardioprotection against reperfusion injury following global ischemia and doxorubicin-induced cardiac damage [17,18]. However, AD 198 is labile to rapid ester hydrolysis of the valerate moiety, resulting in the formation of N-benzyladriamycin (AD 288), a catalytic inhibitor of topoisomerase II with reduced ability to circumvent resistance mediated by multidrug transport proteins or anti-apoptotic protein overexpression [12,19].

The design of more effective treatments for triple-negative breast cancer continues to be challenging, owing to the 1) absence of exploitable receptor targets, as with ER+/PR+ and HER2+ breast tumors, which limits options for targeted therapy [3], and 2) the emergence of chemorefractory cancer cells possessing broad spectrum resistance, which limits the efficacy of current chemotherapeutic agents [2]. Current treatment guidelines for TNBC chemotherapy include the anthracyclines, doxorubicin or epirubicin, in combination with other DNA-damaging and antimicrotubule agents, resulting in an overall objective response rate of 30-50% [3,31]. Exploiting an alternative mechanistic strategy of foregoing the traditional targets of cytotoxic chemotherapy to directly trigger apoptosis via PKCd activation, the inventors surprisingly discovered superiority of the functionally novel anthracycline, pivarubicin and benzarubicin, over the standard-of-care drug, doxorubicin, in the treatment of TNBC.

This background information is provided for the purpose of making information believed by the applicant to be of possible relevance to the present invention. No admission is necessarily intended, nor should it be construed, that any of the preceding information constitutes prior art against the present invention.

BRIEF DESCRIPTION OF THE FIGURES

FIG. 3A shows a detection of proteins by chemiluminescence. FIGS. 3B-3E show microscopy images from detection of DNA fragmentation in pivarubicin-treated 32D.3 cells by TUNEL assay.

FIGS. 7A-7D are bar charts showing results of doxorubicin treatment of TNBC-bearing NSG mice.

FIGS. 9A-9C are microscopy images of representative stained thin sections from a cardiotoxicity analysis of non-tumor-bearing NSG mice. Images show evidence of microvacuolization (small arrows) in both vehicle-treated mice (FIG. 9A) and doxorubicin-treated mice (FIG. 9B). The image in FIG. 9C is from pivarubicin-treated mice.

DETAILED DESCRIPTION

Figure 1B:
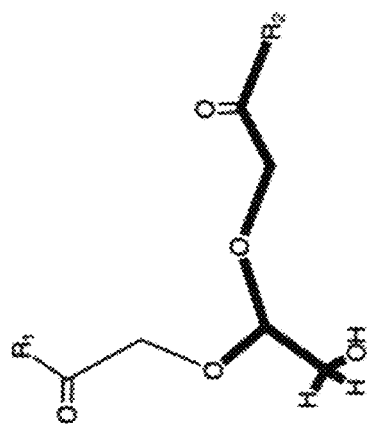
FIGS. 1A-1C show the formulas of pivarubicin (FIG. 1A), diacylglycerol (DAG, FIG. 1B), and phorbol 12-myristate 13-acetate (PMA, FIG. 1C). Bold lines identify the putative pharmacophores (C1b binding site).

For the purposes of promoting an understanding of the principles of the present disclosure, reference will now be made to certain embodiments and specific language will be used to describe the same. It will nevertheless be understood that no limitation of the scope of the invention is thereby intended, and alterations and modifications in the illustrated article of manufacture, and further applications of the principles of the invention as illustrated therein are herein contemplated as would normally occur to one skilled in the art to which the invention relates.

Triple-negative breast cancer (TNBC) is a highly aggressive and distinct subtype that does not express therapeutically exploitable levels of three growth factor receptors (estrogen, progesterone, epidermal growth factor) that are critical for the proliferation of other types of breast cancer. Because of its non-responsiveness to therapy targeting these receptors, TNBC, though comprising only 15% of all breast cancer diagnoses, accounts for 25% of all breast cancer mortality.

Conventional cytotoxic chemotherapies directly or indirectly damaging nucleic acid or inhibiting mitotic spindle function are the current standard of care. This includes systemic cytotoxic drug combinations of anthracyclines, such as doxorubicin ("DOX", Adriamycin™) or epirubicin, taxanes, cyclophosphamide and platinum compounds. Despite initial sensitivity to chemotherapy, TNBC patients experience lower overall disease-free intervals compared with patients whose tumors express sex steroid hormone receptors, with an overall complete remission of only 20-40%. The limited cytotoxic efficacy of chemotherapy is likely due, at least in part, to multiple mechanisms of cellular drug resistance. Therapeutic agents under development target specific components of intracellular proliferative pathways or nucleic acid damage repair machinery in TNBC cells, often in combination with the above conventional drugs. The development of new therapeutic agents that inhibit TNBC cell proliferation in a manner that is unique from those agents that have not been consistently successful in the treatment of TNBC would satisfy a significant unmet clinical need.

Pivarubicin (AD 445) and the closely related benzarubicin (AD 198) are experimental anthracycline drugs with a novel mechanism of cytotoxicity observed in hematological tumor cells; rapid activation of certain isoforms of the signaling enzyme protein kinase C (PKC) and subsequent direct activation of apoptotic programmed cell death. However, as opposed to hematologic tumors and even some hormone receptor-positive breast cancers, activation of certain PKC isoforms in TNBC cells potentiates cell growth, while inhibition of PKC inhibits TNBC cell growth. Based on these observations, it would not be predicted that pivarubicin and benzarubicin would inhibit TNBC tumor growth. The inventors surprisingly found that pivarubicin is a potent inhibitor of TNBC tumor growth, suggesting a novel tumoricidal mechanism that was not obvious in hematological tumors. Pivarubicin has been found to possess a mechanism of action, distinct from that observed in hematologic and hormone receptor-positive breast cancer, that is rapidly effective in blocking the growth of the distinct human tumor sub-type, TNBC.

Definitions

Unless defined otherwise, all technical and scientific terms used herein have the same meaning as commonly understood by one of ordinary skill in the art to which this present disclosure pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise. The use of "a" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

"Treatment" refers to the administration of medicine or the performance of medical procedures with respect to a patient, either for prophylaxis (prevention) or to cure the infirmity or malady in the instance where the patient is afflicted.

A "therapeutically effective amount" is defined herein in relation to the treatment of cancers is an amount that will decrease, reduce, inhibit, or otherwise abrogate the growth of a cancer cell or tumor. Thus, an "effective amount" is the quantity of compound in which a beneficial clinical outcome is achieved when the compound is administered to a subject with a cancer. A "beneficial clinical outcome" includes, for example, a reduction in tumor mass, durable tumor regression a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. The precise amount of compound administered also will depend on the degree, severity and type of cancer.

The skilled artisan will be able to determine appropriate dosages depending on these and other factors.

"Treatment" refers to the administration of medicine or the performance of medical procedures with respect to a patient, either for prophylaxis (prevention) or to cure the infirmity or malady in the instance where the patient is afflicted.

"Cumulative dose" The recommended cumulative doses for doxorubicin and other conventional anthracyclines indicate a maximum that can be given to avoid a significant increase in cardiotoxic effects regardless of whether that cumulative dose was at all effective in treating tumors. If a patient were to relapse after treatment with the maximum cumulative dose of doxorubicin, for example, no further doxorubicin or other cardiotoxic anthracyclines could be administered. In contrast, the estimated cumulative dose of the non-cardiotoxic benzarubicin and pivarubicin compositions of the present disclosure would have a therapeutic effect in regressing the tumor during a course of treatment, rather than a cumulative dose above which cardiotoxic effects become evident. Clinicians could, therefore, choose to administer drug beyond this estimated cumulative dose to achieve tumor eradication without the concern for cardiotoxicity. This is a significant advantage of benzarubicin and pivarubicin over doxorubicin; the fact that the cumulative dose could be much more open ended, allowing for more cycles of treatment and that patients who relapse following the maximum cumulative doses of doxorubicin, daunorubicin or epirubicin can be administered benzarubicin or pivarubicin without risk of cardiotoxicity.

The term "pharmaceutically acceptable salt" refers to those salts of the compounds of the present disclosure which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977), which is incorporated herein by reference in its entirety, for further examples of pharmaceutically acceptable salt). The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, as described in more detail herein below, the hydrochloride salt of the presently disclosed amine-containing anthracycline compounds is made by passing hydrogen chloride gas into an anhydrous solution of the free base. Accordingly, in some embodiments, the pharmaceutically acceptable salt is a hydrochloride salt.

The compositions of the present disclosure may be administered by any suitable route, including, for example, by parenteral administration. Parenteral administration can include, for example, systemic administration, such as by intramuscular, intravenous, intraarterial, subcutaneous, or intraperitoneal injection. The compositions of the present disclosure can also be administered topically, by inhalation (e.g., intrabronchial, intranasal, or intranasal drops), or rectally, depending on the type of cancer to be treated. The compositions of the present disclosure may be delivered regionally to a particular affected region or regions of the subject's body.

The meanings of some abbreviations used in the present disclosure are given in Table 1.

TABLE 1

| Abbreviation | Meaning |
| --- | --- |
| AD 198 | N-Benzyladriamycin-14-valerate |
| | (also known as benzarubicin) |
| AD 288 | N-Benzyladriamycin |
| AD 445 | N-Benzyladriamycin-14-pivalate |
| | (also known as pivarubicin) |
| DOX | Doxorubicin |
| MTD | Maximum tolerated dose |
| pCR | Pathologic complete response |
| PKC | Protein kinase C |
| SOLUTOL | A nonionic surfactant comprising polyethyleneglycol (15)-hydroxystearate |
| TNBC | Triple-negative breast cancer |

Administration of Compositions

Compositions of the present disclosure may be administered systemically as a solution, suspension (such as but not limited to a microsuspension), or emulsion (such as but not limited a microemulsion). Alternatively, the compositions of the present disclosure administered by direct instillation into a body cavity (such as but not limited to intraperitoneally, intrapleurally, intraventricularly as in the brain, and/or rectally as by suppository), inhalation, intravenously, or intramuscularly as a liposomal suspension. When administered through inhalation the active compound or salt should be in the form of a plurality of solid particles (such as but not limited to microparticles) or droplets having a particle size from about 0.5 micrometer to about 5 micrometers, and preferably from about 1 micrometer to about 2 micrometers.

Benzarubicin may be administered for the treatment of TNBC in an amount of 1 mg/mL. Similarly, and pivarubicin may be administered for the treatment of TNBC in an amount of 1 mg/mL.

Furthermore, a composition comprising at least one of pivarubicin and benzarubicin may be used either as first-line TNBC therapy as a replacement for doxorubicin, or in adjuvant or neo-adjuvant therapy or for salvage therapy in relapse patients who cannot be administered any additional doxorubicin due to cardiotoxicity concerns. As for co-administration, the compositions of the present disclosure may be administered either with currently used TNBC drugs such as docetaxel, carboplatin, capecitabine, eribulin, gemcitabine and vinorelbine or other cancer targeted agents.

Dose Range and Schedule

The composition of the present disclosure (for pivarubicin and benzarubicin) may be provided for the treatment of TNBC in humans and mammals, including, for example dogs (canines) and cats (felines), as shown in Table 2.

TABLE 2

| Mammal | Low | Median | High |
|---|---|---|---|
| Human | 0.7 mg/Kg (52 mg/m$^2$) | 1.4 mg/Kg (52 mg/m$^2$) | 2.8 mg/Kg (52 mg/m$^2$) |
| Canine & Feline (exemplary embodiments) | 1.4 mg/Kg (52 mg/m$^2$) | 2.8 mg/Kg (54 mg/m$^2$) | 5.6 mg/Kg (52 mg/m$^2$) |

The composition according to the present disclosure may be administered every 10-21 days.

Benzarubicin (N-benzyladriamycin-14-valerate, AD 198) can undergo enzymatic and non-enzymatic ester hydrolysis to release the valerate moiety to form AD 288. AD 288 is a comparable cytotoxic compound, however, the cytotoxicity occurs through a mechanism that is distinct from benzarubicin, pivarubicin, as well as the commonly used antitumor agent, doxorubicin. One limitation of AD 288 is that it cannot bypass the mechanisms of drug resistance that benzarubicin, while pivarubicin can. Pivarubicin (N-benzyladriamycin-14-pivalate, AD 458) is more resistant to hydrolysis, since the pivalate moiety sterically shields the ester linkage.

Examples of nonlimiting embodiments of the present disclosure are included immediately below.

Embodiment 1. A method for treating triple negative breast cancer (TNBC), said method comprising administering to a subject an effective amount of at least one of pivarubicin and benzarubicin, or a pharmaceutically acceptable salt thereof.

Embodiment 2. The method of embodiment 1, wherein said subject is a mammal (e.g., any of human, canine, and feline).

Embodiment 3. The method of any of the preceding embodiment, wherein treating TNBC further comprises inhibition of tumor growth.

Embodiment 4. A composition comprising at least one of pivarubicin and benzarubicin, or a pharmaceutically acceptable salt thereof, and a nonionic surfactant.

Embodiment 5. The composition of embodiment 4, wherein said nonionic surfactant is polyethyleneglycol (15)-hydroxystearate (also known as SOLUTOL, macrogol (15)-hydroxystearate, or KOLLIPHOR HS 15).

Embodiment 6. The composition of embodiment 5, wherein said composition further comprises an alcohol (such as ethanol).

Embodiment 7. The composition of any of embodiments 4-6, wherein the nonionic surfactant is present in an amount of 0.1% to 1.0%.

Embodiment 8. The composition of any of embodiments 4-6, wherein the nonionic surfactant is present in an amount of about 0.1%.

Embodiment 9. The composition of any of embodiments 4-6, wherein the nonionic surfactant is present in an amount of about 0.125%.

Embodiment 10. The composition of any of embodiments 4-9, wherein the pivarubicin is present in an amount of about 0.5-3.0 mg/mL, preferably 0.75-2.5 mg/mL.

Embodiment 11. The composition of any of embodiments 4-9, wherein the benzarubicin is present in an amount of about 0.5-3.0 mg/mL, preferably 0.75-2.5 mg/mL.

Embodiment 12. The composition of embodiments 4-9, wherein the pivarubicin is present in an amount of about 1 mg/mL.

Embodiment 13. The composition of any of embodiments 4-9, wherein the benzarubicin is present in an amount of about 1 mg/mL.

Embodiment 14. The composition of any of embodiments 4-13, wherein said composition formulated for parenteral administration.

Embodiment 15. A method for treating triple negative breast cancer (TNBC), said method comprising administering to a subject an effective amount of a composition of any of the preceding embodiments.

Embodiment 16. The method of embodiment 15, wherein said amount is about 1 mg/mL.

Embodiment 17. The method of embodiment 15, wherein the pivarubicin is present in an amount of about 300-750 mg cumulative dose, with a preferred range of 300-400 mg.

Embodiment 18. The method of embodiment 15, wherein the benzarubicin is present in an amount of about 300-750 mg cumulative dose, with a preferred range of 300-400 mg.

Embodiment 19. The method of any of embodiments 1-3 and 15-18, wherein the at least one of pivarubicin and benzarubicin is provided in a composition comprising 10%-30% ethanol and 70%-90% sterile saline.

Embodiment 20. The method of any of embodiments 1-3 and 15-18, wherein the at least one of pivarubicin and benzarubicin is provided in a composition comprising about 20% ethanol and about 80% sterile saline, and further comprising about 0.125% SOLUTOL.

Embodiment 21. The method of any of embodiments 1-3 and 15-18, wherein the at least one of pivarubicin and benzarubicin is provided in a composition comprising 10%-30% ethanol and 70%-90% sterile saline, and SOLUTOL.

Embodiment 22. The composition of embodiment 9, wherein the nonionic surfactant is present in an amount of about 0.5%

Embodiment 23. In some further embodiments, the present disclosure pertains to compositions comprising at least one of pivarubicin and benzarubicin, alcohol, and a nonionic surfactant (e.g., SOLUTOL) in an amount of at least about 0.125%. Nonionic surfactant (e.g., SOLUTOL) may be used in the composition in an amount of at least at least 0.1-10%, 0.1-0.5%, 0.1-1.0%, 0.1-3.0%, and even 0.1-5.0%.

EXAMPLES

Methods
Chemicals and Biologicals

Pivarubicin used for TNBC studies was synthesized by Dr. John Rimoldi (Univ. of Mississippi) using the previously described protocol [20,21]. Doxorubicin HCl, rottlerin and all antibodies were purchased from Sigma-Aldrich (St. Louis, Mo.). For in vitro experiments, doxorubicin and pivarubicin were dissolved in DMSO. The final maximum DMSO concentration used for in vitro drug treatments (1% for 72 hours) was not cytotoxic. IL-3-dependent 32D.3 murine myeloid cells, CCRF-CEM human lymphoblastic leukemia cells and multidrug-resistant variants (generous gift of Dr. William T. Beck, St. Jude Children's Research Hospital, Memphis, Tenn.), 293 embryonic human kidney cells and HL-60 human acute myeloid leukemia cells transfected with Bcr-Abl, Bcl-$X_L$ or empty expression vectors (generous gift of Dr. Kapil Bhalla, Univ. of Miami) were maintained as previously described [12,14,22,23]. K562 human chronic myelogenous leukemia and LNCaP human prostate cancer cells were purchased from ATCC (Manassas, Va.) and maintained as described by the vendor. LNCaP/Bcl-2 cells were the generous gift of Dr. Ralph Buttyan (Columbia Univ.). Luminescent MDA-MB-231-LM2 (LM-2; metastatic lung subpopulation isolated from human TNBC MDA-MB-231 cells transduced with eIF1a-Luc2-puro lentivirus) were generously provided by Dr. Yibin Kang, Princeton Univ.) and maintained in culture as previously described [24]. PKCd siRNA [25] and scrambled variant were obtained from Qiagen (Germany).

Drug Biotransformation Analysis

Quantitative and qualitative determination of AD 198 and pivarubicin biotransformation was determined by reverse-phase HPLC as described previously [26,27].

Fluorescence Microscopy 32D.3 cells were grown in suspension culture in the absence of drug for 24 h prior to analysis. Cells at a density of $1 \times 10^6$/mL were exposed to 5 µM doxorubicin or 1 µM pivarubicin for 1 hour, then harvested, washed and resuspended in phosphate-buffered saline, pH-7.2 (PBS). Nuclear counterstaining of pivarubicin-treated cells was performed by treatment of cells with 16 µg/mL bisbenzimide for 1 hour. Drug autofluorescence was observed with an Olympus BH-2 phase-contrast microscope with a mercury UV light source under UV illumination (red: excitation filter, 530-560 nm; barrier filter, 580 nm; blue: excitation filter (340-390 nm) at ×1000 magnification.

Analysis of Apoptosis

Detection of DNA fragmentation in apoptotic cells by the TUNEL assay and immunoblot analyses of cytochrome c release were performed as described previously [12].

PKC Inhibition, Cell Viability Determinations and Immunoblot Analysis.

Rottlerin treatment of cells, cell viability analysis by MTT [28] and immunoblot identification of protein expression were performed and described previously [12].

Injection of Cells into the Murine Mammary Fat Pad

Monolayer LM2 cells were trypsinized and resuspended in DMEM media containing 10% FBS and 1× antibiotic/antimitotic. Cell concentration was adjusted to yield 2.5 105 cells for each 10 uL injection in PBS. After preparation for injection, cells were kept on ice at all times. Cells were surgically implanted into the left and right inguinal mammary glands of 4-week-old female NSG mice (NOD/SCID IL2Rγ−/−; Jackson Laboratory [Bar Harbor Me.] #5557) bred in-house. Mice were anesthetized with 1.2% avertin via intraperitoneal (i.p.) injection prior to surgery. Mice were also injected subcutaneously between shoulder blades with rimadyl for pain relief on day of surgery and on day following surgery. Primary tumor growth prior to and during treatment was monitored initially by manual palpation for tumor appearance, then twice weekly using digital calipers. Tumor volume was calculated by the formula: Volume=(Width2×Length)/2. When tumors attained a volume of approximately 150-190 mm², cohorts of 10 randomized drug-naïve, female, NSG mice (8±1 weeks old, 23±2 g) were administered the maximum tolerated dose (MTD) of pivarubicin, doxorubicin or the equivalent volume of vehicle (70% sterile saline, 15% ethanol, 15% Cremophor EL) as a bolus i.p. injection in parallel experiments. Tumor volumes were measured in a blinded manner.

All procedures were done in sterile cabinet. At termination of experiments, mice were sacrificed humanely by $CO_2$ inhalation followed by cervical dislocation. Animals were housed in a closed-barrier facility using an Optimice cage system (Animal Care Systems, Inc., Centennial, Colo.) housed on a carousel with "Bed-O'-Cobs" bedding material (The Andersons Lab Bedding Products, Maumee, Ohio).

Animals were housed up to 10 mice per cage. In-house breeding was performed by a trio mating (1 male to 2 females) scheme (12 h light/dark cycle, avg. temp ~21° C.). All mice were maintained on a 7904 irradiated high fat diet (Teklad, Madison, Wis.). Food/water was provided ad libitum. Domes and craft paper nests provided for enrichment. Animal health was monitored by visual observation supplemented by body condition scoring as well as weight loss (greater than 20%, as animals approached endpoints, measuring 2-3×/wk) to monitor endpoint. All animal procedures were approved by the Institutional Animal Care and Use Committee at the University of Tennessee Health Science Center as accredited by the Association for the Assessment and Accreditation of Laboratory Animal Care.

Imaging Mice Using In Vivo Imaging System.

Mice were imaged using Xenogen In Vivo Imaging System® Lumina from Perkin Elmer (Waltham Mass.). Stock D-Luciferin, Firefly, potassium salt (Perkin Elmer, 122799) was prepared in DPBS at a concentration of 30 mg/mL and sterile filtered with 0.2 micrometer syringe filter. Luciferin was further diluted to 15 mg/mL in DPBS prior to injection. Mice were injected i.p. with 200 uL of luciferin. Primary tumors were imaged by placing mice in dorsal recumbency using luminescent setting of auto exposure, field of view D with resolution setting of 4 (medium binning), 10 minutes after injection with luciferin, approximately 5 minutes following anesthetization with isoflurane. Data are reported as total flux in photons per second (p/s) using Living Image software.

Cardiotoxicity Assessment.

Drug-mediated cardiotoxicity was assessed in both non-tumor-bearing female NSG mice administered three doses (i.p. every two weeks) of the MTD of doxorubicin, pivarubicin or the equivalent volume of solvent only and in hearts excised from tumor-bearing mice treated as described in Results section. Body weights were monitored every three days. Two weeks after final dose, mice were sacrificed, and hearts were excised immediately. Intact ventricular myocardia were fixed for a minimum of 24 h in 10% formalin phosphate buffered to pH 7.0 and then carefully sectioned into 2 to 3-mm thick slices before being dehydrated in graded ethanol and cleared in xylene prior to embedding in paraffin at 58° C. Sections (4-µm thick) were mounted on glass slides, deparaffinized in xylene, and stained in the routine fashion with Mayer's hematoxylin and eosin. Slide labels were blinded to evaluator. Myocardial lesions were evaluated by routine light microscopy and scored with regard to the severity and extent of damage [29]:

Degree of severity (S)—0, no evidence of histological changes; 1, sarcoplasmic microvacuolization and/or inclusions (interstitial or cellular edema); 2, as in 1 plus sarcoplasmic macrovacuolization or atrophia, necrosis, fibrosis, endocardial lesions, and thrombi.

Degree of extension (E)—0, no lesions; 0.5, less than 10 single altered myocytes on the whole-heart section; 1, scattered single altered myocytes; 2, scattered small groups of altered myocytes; 3, spread small groups of altered myocytes; 4, confluent groups of altered myocytes; 5, most of cells damaged.

Total cardiotoxicity score/animal=S×E and mean total score (MTS) for each treatment group was MTS=(S×E)/number of animals.

Results

Figure 1C:
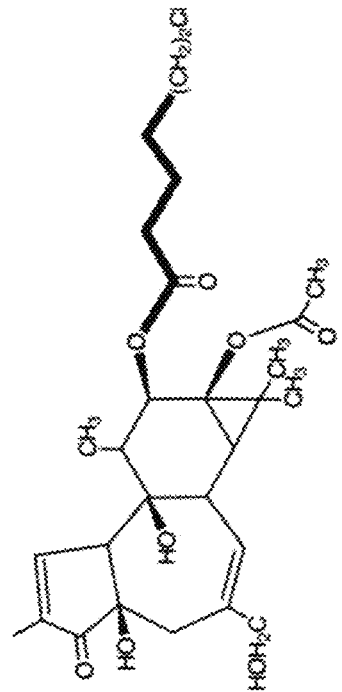
Figure 1A:
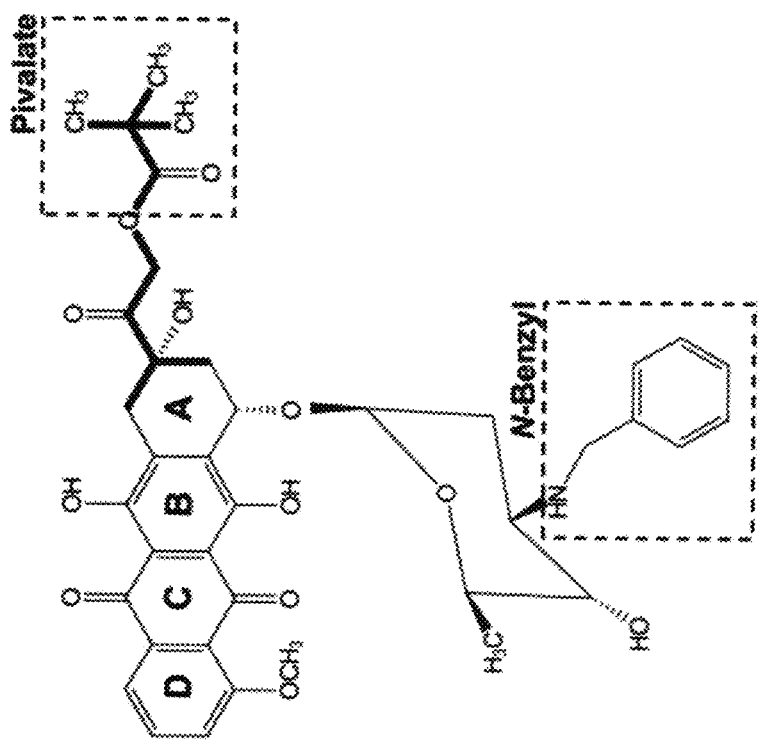

Pivarubicin (FIG. 1A) was designed to be a hydrolytically stable congener of our previously developed anthracycline antitumor compound, AD 198. In contrast to the straight-chain 5-carbon valerate moiety at C-14 appended to the anthraquinone A ring through an esterase-labile ester linkage in AD 198, pivarubicin contains a tertiary trimethyl (pivalate) moiety at the same site that is proposed to sterically hinder enzyme-mediated ester hydrolysis yet retains the 3-dimensional configuration that mimics the C1b regulatory domain ligands, diacylglycerol (FIG. 1B) and phorbol 12-myristate 13-acetate (FIG. 1C) [11]. In FIGS. 1A-1C, bold lines identify putative pharmacophores (C1b binding site) for these compounds. Resistance of the pivalate moiety in pivarubicin to hydrolysis is confirmed following treatment of 32D.3 murine myeloid cells, J774.2 murine macrophage-like cells and 293 embryonic human kidney cells with pivarubicin and AD 198 at 1 μM for 1 hour, followed by qualitative and quantitative analysis of drug content by reversed-phase HPLC [26,27].

While AD 198 was subject to approximately 50% biotransformation to N-benzyladriamycin (AD 288) 8 hours after drug uptake into cells, less than 10% of pivarubicin was initially biotransformed and showed little time-dependent conversion to AD 288. Cells at a density of $1 \times 10^6$ cells/mL were treated with 1 μM drug (AD 198 or pivarubicin) at 37° C. for 1 hour, then harvested immediately or incubated for an additional 7 hours in drug-free medium. Intracellular drug was extracted and analyzed by fluorescence HPLC as described previously [26,27]. AD 198 and pivarubicin biotransformation was represented by the percentage of intact intracellular drug remaining. Results were as summarized in Table 3.

TABLE 3

| | % Parent Compound | | | | | |
|---|---|---|---|---|---|---|
| | 32D.3 | | 293 | | J774.2 | |
| | 1 hr | 8 hr | 1 hr | 8 hr | 1 hr | 8 hr |
| AD 198 | 90 | 56 | 80 | 50 | 90 | 50 |
| Pivarubicin | 100 | 96 | 98 | 94 | 90 | 90 |

Figure 2A:
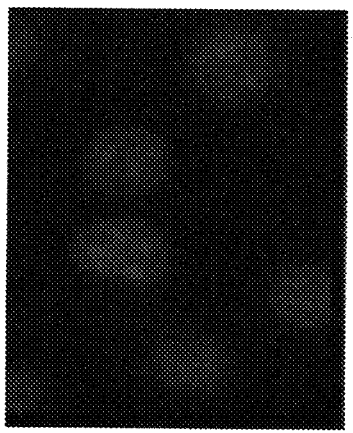
FIGS. 2A-2C are fluorescence microscopy images from a study of cellular localization of pivarubicin.
Figure 2B:
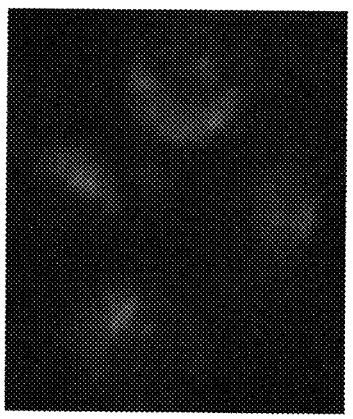
Figure 2C:

Possessing a hydrolytically stabile C-14 moiety, pivarubicin retained the functional characteristics initially described for AD 198, including rapid cellular uptake and localization almost exclusively in the perinuclear region of the cytoplasm (FIGS. 2A-2C) under three conditions: In one example, 32D.3 cells at a density of $1 \times 10^6$/mL were exposed to 5 μM doxorubicin (FIG. 2A), and in another example the cells were exposed to 1 μM pivarubicin for 1 hour (FIG. 2B). Nuclear counterstaining of pivarubicin-treated cells was performed with 16 μg/mL bisbenzimide for 1 hour (FIG. 2C). Fluorescence microscopy was performed as described in Materials and Methods. Images are at ×1000 magnification.

Once distributed into microsomal membranes, pivarubicin triggered rapid, mitochondrial-dependent apoptosis that was independent of cell cycle arrest. Marked release of cytochrome c into the cytosol as an indicator of mitochondrial depolarization and dysfunction is detected within 5 hours of drug treatment, while DNA fragmentation, as detected by TUNEL staining, is abundant by 6 hours.

Figure 3A:
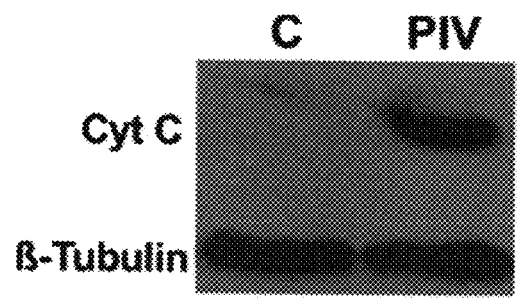
FIGS. 3A-3E are images from studies of Pivarubicin-mediated rapid apoptosis.
Figure 3B:
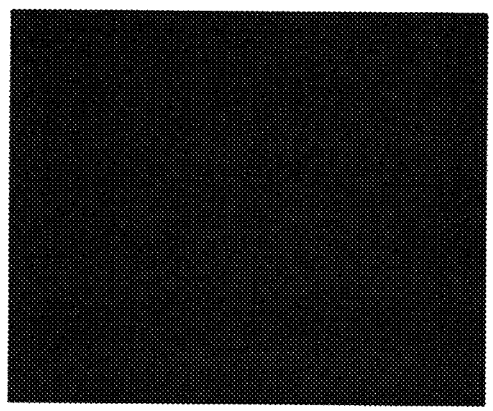
Figure 3C:
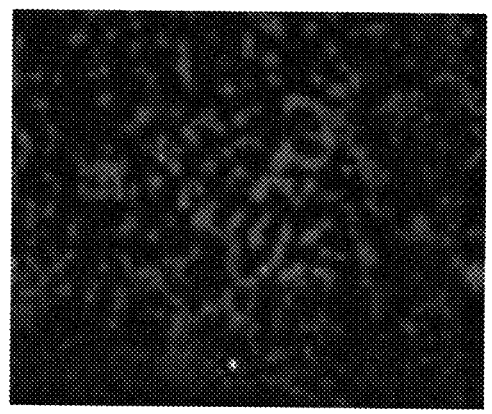
Figure 3D:
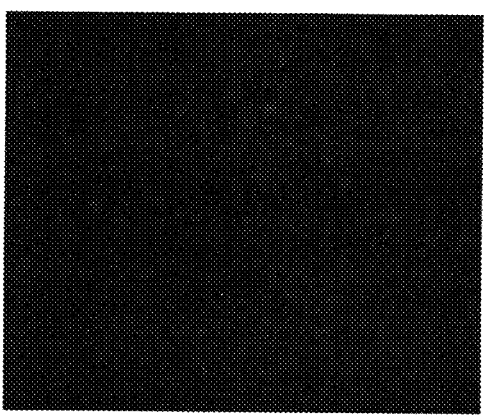
Figure 3E:
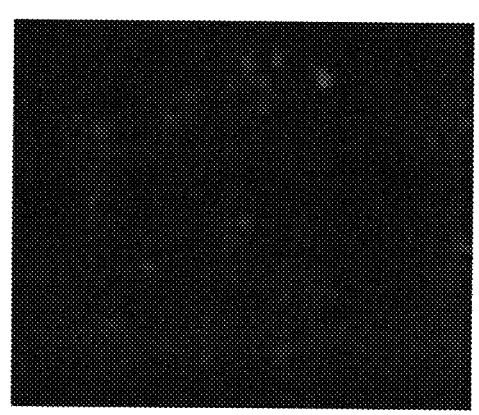

In a study of Cytochrome c (Cyt C) release by pivarubicin (PIV) and control (C), 32D.3 cells were exposed to 5 μM pivarubicin for 1 hour, then incubated in drug-free medium for an additional 4 hours. Cells were then fractionated to isolate the cytosolic fraction, subjected to immunoblotting and treated with anti-cytochrome c monoclonal antibody (1:250) for 2 hours, followed by a 1-hour treatment with 1:1000 dilution of horseradish peroxidase-conjugated goat anti-mouse second antibody as described previously [12]. Proteins were detected by chemiluminescence (FIG. 3A). FIGS. 3B-3E show images of detection of DNA fragmentation in pivarubicin-treated 32D.3 cells by TUNEL assay. Cells were treated with 5 μM pivarubicin for 1 hour, washed twice in warm PBS, incubated in drug-free medium for 6 hours, then prepared for 3'-biotinylation of fragmented DNA using the TUNEL assay procedure. Individual fields of cells were detected for both DNA 3'-end labeling (green: grayscale image in FIG. 3D) or total cellular DNA staining by propidium iodide (red: grayscale images in FIGS. 3C and 3E). Composite image is representative of three independent experiments.

Consistent with the computer modeling and binding studies of N-benzylanthracyclines with varying C-14 acyl chain length and conformation with the C1b regulatory of PKC [10,11], pivarubicin-induced cytotoxicity is dependent on PKCd activation.

FIGS. 4A-4D are charts and images from studies of pivarubicin cytotoxicity mediated through PKC-delta (PKCd) activation. For FIG. 4A, 32D.3 cells, suspended in RPMI-1640 medium/10% FCS/IL-3 at a density of 5×105 cells/ml, were treated with either DMSO (C) or 5 μM pivarubicin (PIV) for 4 h prior to harvesting, cell fractionation, and immunoblot analysis of PKCd as described previously [14]. For FIG. 4B, 32D.3 cells were pretreated with 10 μM rottlerin for 2 h prior to exposure to 5 μM drug for 1 h at 37° C. Cells were pelleted and washed twice in large volumes of warm PBS, then resuspended in fresh, drug-free medium containing 10 μM rottlerin at 5×105 cells/ml and incubated at 37° C. for up to 72 h. At indicated times, aliquots of cells were withdrawn and stained with trypan blue. Viable cells were scored based on the exclusion of stain and gross morphological appearance. For the results shown in FIGS. 4C and 4D, 32D.3 cells were transfected with PKCd siRNA or scrambled siRNA as described in the Materials and Methods section under "Chemicals and Biologicals". The cells were then assessed for pivarubicin cytotoxicity as for FIG. 4A. Each datum point represents the mean and standard error of at least three independent determinations, each consisting of 300-500 cells per count, when possible.

Figure 4A:
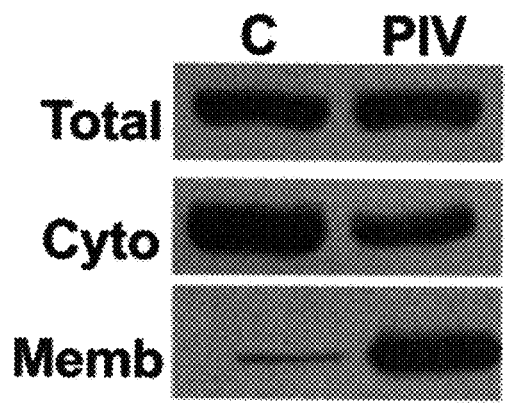
FIGS. 4A-4D are charts and images from studies of pivarubicin cytotoxicity mediated through PKC-delta (PKCd) activation.
Figure 4B:
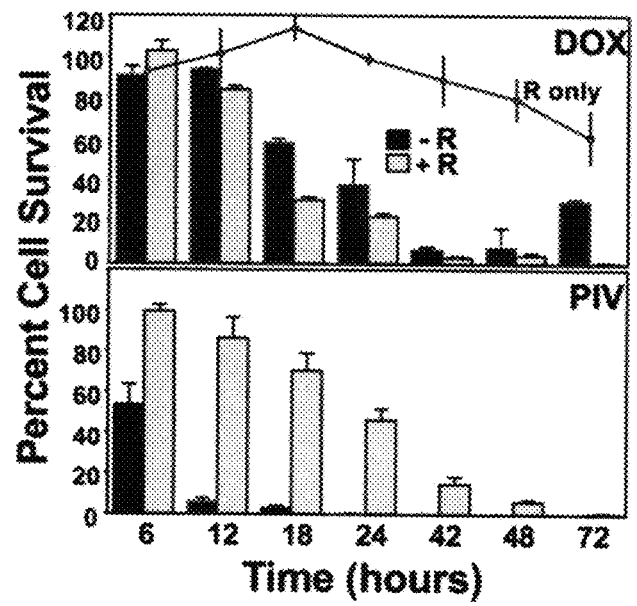
Figure 4C:
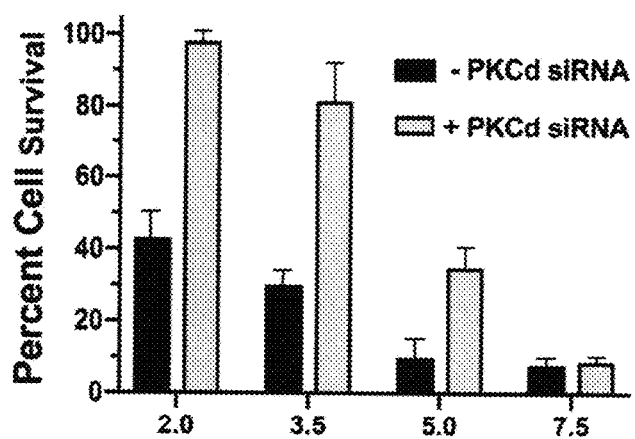
Figure 4D:
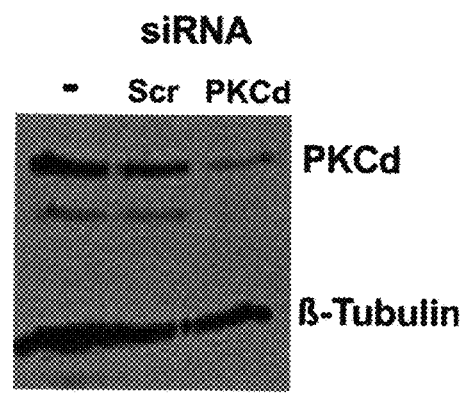

Within 4 hours of treatment with 5 μM pivarubicin, PKCd translocates from the cytosolic to the membrane fraction of 32D.3 cells, consistent with PKCd activation (FIG. 4A). Inhibition of PKCd activity also selectively impedes pivarubicin cytotoxicity. Treatment of cells with the $IC_{50}$ concentration of doxorubicin produces a progressive decrease in the viable cell population down to 50% by 24 hours of drug treatment. Co-treatment of cells with rottlerin, a selective inhibitor of the pro-apoptotic PKCd, does not alter doxorubicin cytotoxicity. However, while pivarubicin produces 50% cell kill within 6 hours of treatment, rottlerin markedly delays pivarubicin 50% cell kill to 24 hours (FIG. 4B). Likewise, downregulation of PKCd expression in human LNCaP prostate cancer cells by PKCd siRNA transfection inhibits pivarubicin-mediated cell kill, with a 2.5-fold increase in pivarubicin concentration required to achieve 50% cell kill in PKCd-siRNA-transfected cells, thus supporting PKCd activation by pivarubicin as the trigger for apoptosis (FIGS. 4C and 4D).

In addition to its novel mechanisms of cytotoxic action, pivarubicin circumvents multiple mechanisms of cellular drug resistance. CCRF-CEM cells selected for resistance to vinblastine (CEM/VLB-10 and CEM/VLB-100) overexpress P-glycoprotein, exhibit 10.6- and 269-fold resistance to vinblastine [22] and exhibit 12- and 73-fold resistance to doxorubicin, respectively. However, VLB-10 cells exhibit no resistance to pivarubicin, and VLB-100 cells are only 3-fold resistant.

Figure 5A:
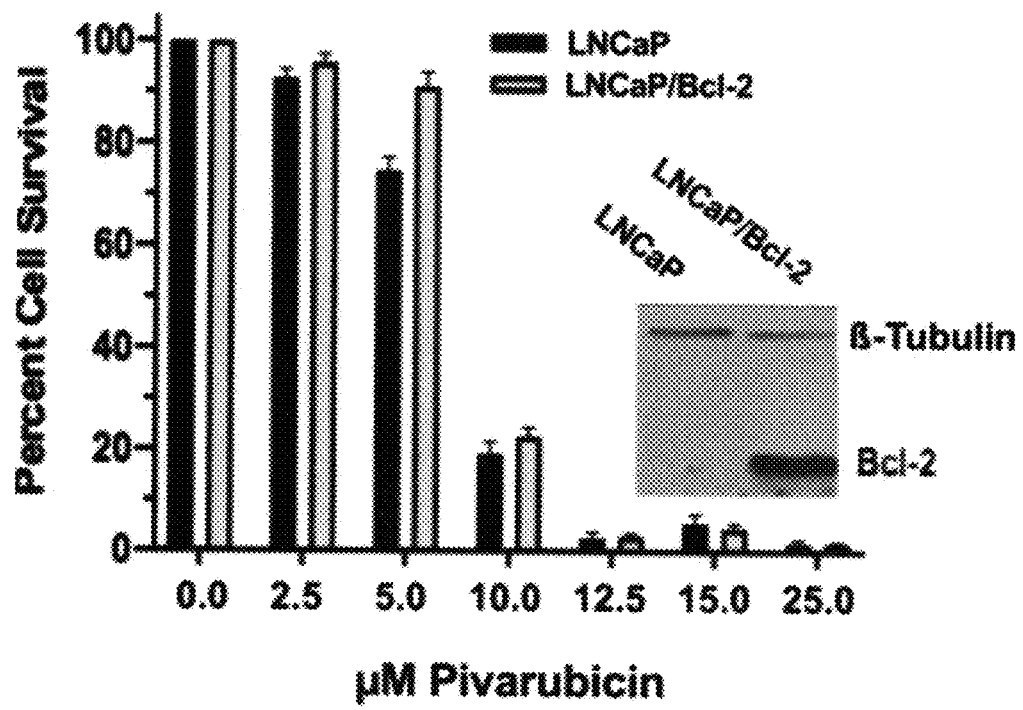
FIGS. 5A and 5B are charts from studies of pivarubicin circumventing multiple mechanisms of MDR.

Overexpression of transfected anti-apoptotic proteins Bcl-2 in LNCaP human prostate cancer cells (FIG. 5A) and Bcl-$X_L$ in HL-60 human promyelocytic leukemia cells (FIG. 5B) do not impede the rate of pivarubicin-induced apoptosis. For the results shown in FIG. 5A, LNCaP cells transfected with Bcl-2 expression vector were assessed for doxorubicin or pivarubicin cytotoxicity, compared to cells transfected with empty vectors. Cells were exposed to 5 μM drug for 1 h, washed, and further incubated for 72 h in drug-free medium. Viability was determined by the MTT assay. For the results shown in FIG. 5B, pivarubicin cytotoxicity in HL-60 cells transfected with Bcr-Abl or Bcl-XL expression vectors were assessed for doxorubicin or pivarubicin cytotoxicity and compared as described for FIG. 5A. Each datum point represents the mean and standard error of at least three independent determinations.

Figure 5B:
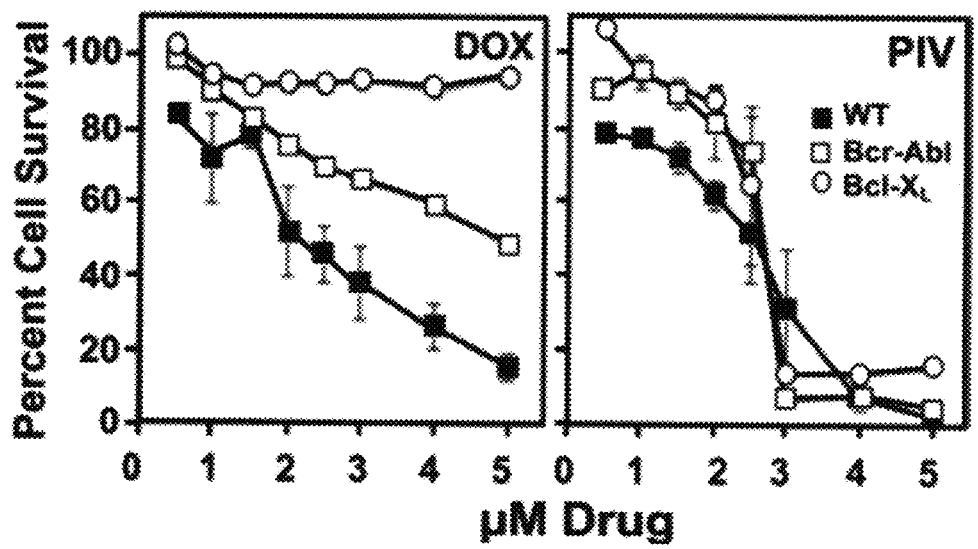

The oncogenic fusion protein, Bcr-Abl, had no inhibitory effect on pivarubicin cytotoxicity in HL-60 cells, in contrast to doxorubicin (FIG. 5B). In total, these cell-based results indicate that similar to its more chemically labile congener, AD 198, the rapid uptake of pivarubicin in mammalian cells, which is unaffected by P-glycoprotein expression, results in cytoplasmic localization of drug, rapid translocation and activation of PKCd to trigger mitochondrial-dependent apoptosis in a manner that does not require prior cell cycle arrest and is not impeded by the overexpression of anti-apoptotic proteins.

Figure 6B:
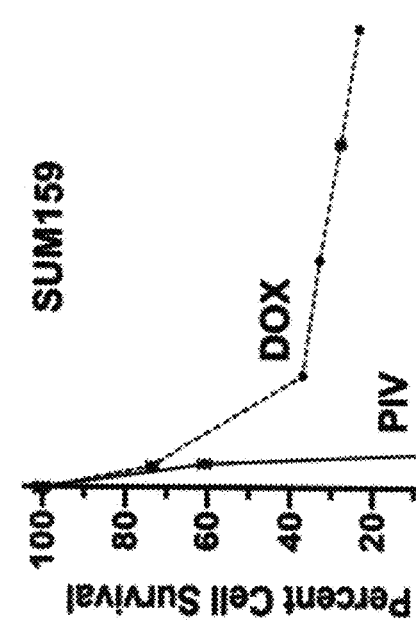
FIGS. 6A-6F are charts and microscopy images for results from a study of whether pivarubicin is more cytotoxic than doxorubicin against triple-negative breast cancer (TNBC) monolayer cells and tumorspheres.
Figure 6A:
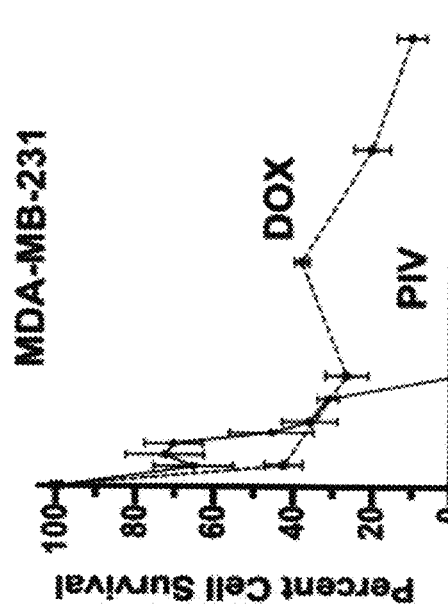

Based upon the ability of pivarubicin to circumvent multiple mechanisms of resistance against doxorubicin, we then examined the efficacy of pivarubicin against TNBC in comparison to doxorubicin, using the following procedure, using two basal TNBC cell lines. MDA-MB-231 cells and SUM-159 cells were maintained under adherent monolayer growth conditions. Upon reaching 50% confluency, cells were treated for 48 h with the dose range of doxorubicin or pivarubicin as indicated in FIGS. 6A and 6B. Cell viability was corrected for death observed in vehicle-only-treated cells (<1% ethanol final well concentration).

Figures 6C, 6D, 6E, 6F:
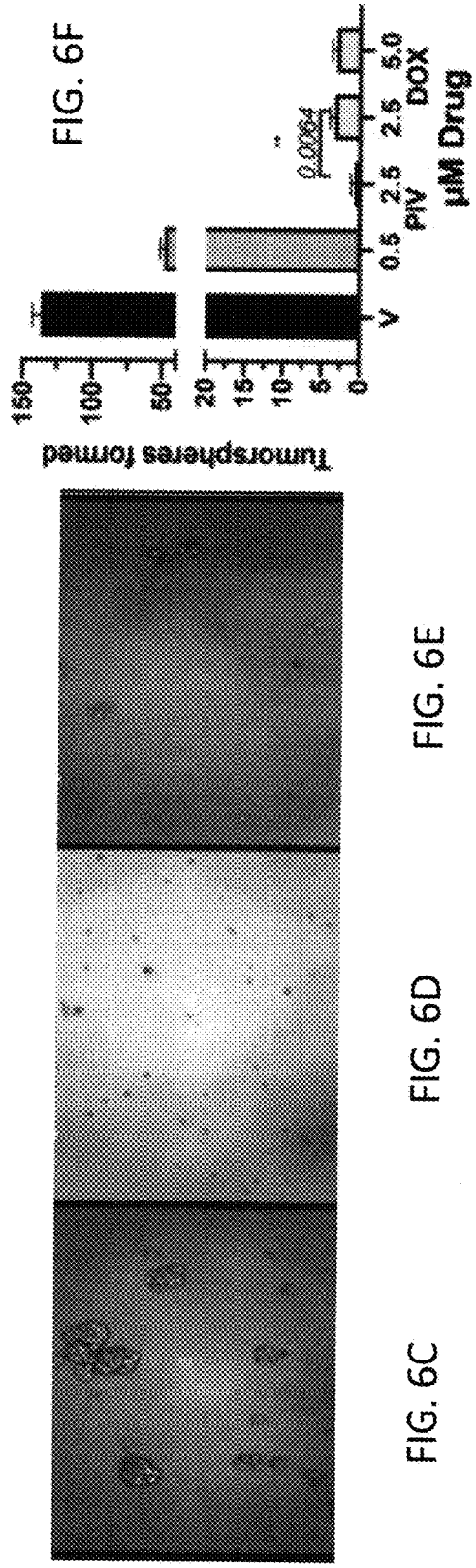

MDA-MB-231 monolayer culture was plated at 6,500 cells per well into a 24-well ultralow adhesion dish in tumorsphere medium with either vehicle, pivarubicin (NV), or doxorubicin (DOX), and cultured for up to 7 days prior to obtaining the digital images shown in FIG. 6C (vehicle only), FIG. 6D (2.5 uM PIV), and FIG. 6E (2.5 uM DOX). The bar graph in FIG. 6F represents the mean number of tumorspheres greater than 50 nm in diameter/well (n>3).

Both cell lines exhibit a biphasic response to doxorubicin in MTT assays, with IC50 concentrations for MDA-MB-231 and SUM159 cells of 1 μM and 4 respectively (FIGS. 6A and 6B). However, the remaining cell subpopulations were significantly less sensitive to doxorubicin, ultimately shifting the $IC_{90}$ concentrations to >20 μM in both cell lines. In contrast, response to pivarubicin treatment was largely monophasic in both cell lines, with $IC_{50}$ concentrations of 2.5 μM and 1.5 and $IC_{90}$ concentrations of 4.5 μM and 1.7 μM in MDA-MB-231 and SUM159 cells, respectively. Consistent with monolayer cell culture results, pivarubicin was significantly more effective than doxorubicin in preventing secondary tumorsphere formation by MDA-MB-231 cells, with complete inhibition with 2.5 μM pivarubicin, but only partial inhibition by 2.5 μM doxorubicin (FIG. 6F). Similar results were observed with SUM159 tumorspheres (not shown).

The superiority of pivarubicin over the commonly used antitumor agent, doxorubicin in our in vitro findings led us to investigate whether pivarubicin demonstrates therapeutic superiority in vivo. In the absence of specific receptor targets, the current treatment of metastatic TNBC relies on doxorubicin-based multidrug therapy, with only limited effectiveness. MDA-MB-231 is a highly aggressive, metastatic, and poorly differentiated claudin-low human TNBC cell line that has been used extensively as a model for drug response and resistance [30]. Cytotoxicity (MTT) assays comparing cultured MDA-MB-231 cell treated with pivarubicin and doxorubicin (48-hour continuous exposure) demonstrated a pivarubicin $IC_{90}$ of 5.1 μM versus 20.0 μM for doxorubicin, supporting the prediction of greater in vivo efficacy of pivarubicin over doxorubicin. Subsequently, we determined whether pivarubicin is therapeutically superior to doxorubicin in vivo by using an orthotopic xenograft model of luminescent MDA-MB-231 cells (LM2) engrafted into the left and right inguinal mammary glands of female NSG mice. Once achieving a primary tumor volume of 150-190 mm³, mice were randomized into three cohorts for treatment with the MTD of pivarubicin or doxorubicin, or the equivalent volume per body weight of vehicle.

The MTD of pivarubicin and doxorubicin, as determined in 8-week-old non-tumor-bearing female NSG mice, was defined as the dose given i.p. (rapid push in 70% sterile saline, 15% EtOH, 15% Cremophor EL) once every 2 weeks (two doses) that produced a maximum reversible 20% decrease in mean body weight. A doxorubicin dose of 1.4 mg/kg resulted in a reversible mean weight loss of 22% after 3 prior escalating doses. In an independent dosing experiment, 1.8 mg/kg resulted in an irreversible mean weight loss of >25%. The MTD for pivarubicin was 26.6 mg/kg, producing a reversible mean 20% weight loss after two doses, with a third dose producing an irreversible mean weight loss >20%.

In a study of doxorubicin treatment of TNBC-bearing NSG mice, LM2 cells were implanted into the 4R and 4L cleared mammary fat pads of female NSG mice and permitted to proliferate for 26 days until a tumor volume range of 125-190 mm3 was reached based on caliper measurements. Doxorubicin was administered IP rapid push in 70% sterile saline, 15% EtOH, 15% Cremophor EL at 14-day intervals, with tumor volumes measured at indicated days post-implantation, as summarized in FIG. 7A. Dosing was suspended at 47 days due to tumor size. At endpoint, mice were euthanized, and primary tumors resected for volume (FIG. 7B), weight (FIG. 7C), and luminescence (FIG. 7D) measurements. Endpoint results are expressed as the mean±standard error of 10 mice per group. Statistical significance was determined by the Wilcoxon rank-sum test.

Primary LM2 tumors treated with either a single MTD of 1.4 mg/kg or a second escalated dose of 1.6 mg/kg DOX 14 days later failed to exhibit reduced growth compared with vehicle treatment, as indicated by tumor volume measurements during treatment (FIG. 7A) or endpoint volume (FIG. 7B) and weight (FIG. 7C) determinations of excised tumors. Luminescence comparison of doxorubicin- and vehicle-treated primary tumors demonstrated similar flux (FIG. 7D), suggesting that both groups of tumors had comparable quantities of live cells. Further dosing with DOX was precluded by excessive and irreversible weight loss in tumor-bearing mice.

Pivarubicin treatment of TNBC-bearing NSG mice was also studied. LM2 cells were implanted into the 4R and 4L cleared mammary fat pads of female NSG mice and permitted to proliferate for 22-24 days until a tumor volume range of 125-190 mm3 was reached based on caliper measurements. Pivarubicin was administered IP rapid push in 70% sterile saline, 15% EtOH, 15% Cremophor EL as either a single dose at 26.6 mg/kg (FIG. 8A) or in two 16.5-mg/kg doses at a 14-day interval (FIG. 8B) with tumor volumes measured at indicated days post-implantation. Dosing was suspended at 47 days due to tumor size in vehicle-treated mice. At endpoint, mice were euthanized, and primary tumors resected for volume (FIG. 8C) and weight (FIG. 8D) measurements. Results are expressed as the mean±standard error of 10 mice per group. Statistical significance was determined by the Wilcoxon rank-sum test.

Figure 8A:
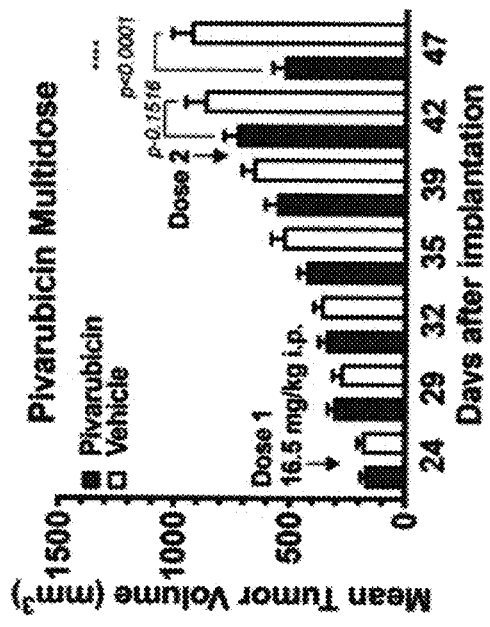
FIGS. 8A-8D are bar charts showing results of pivarubicin treatment of TNBC-bearing NSG mice.
Figure 8B:
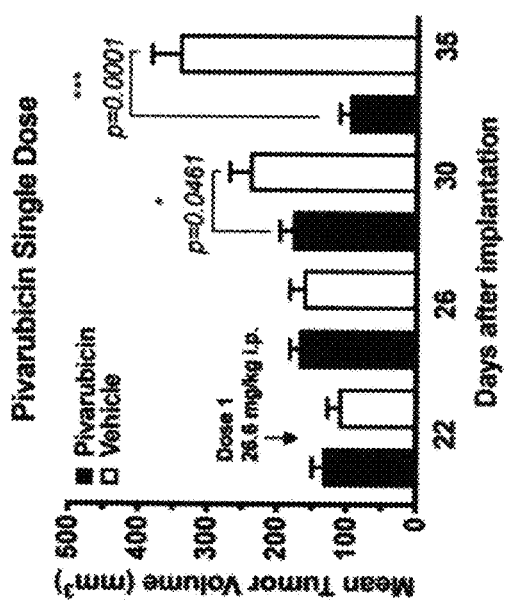
Figure 8C:
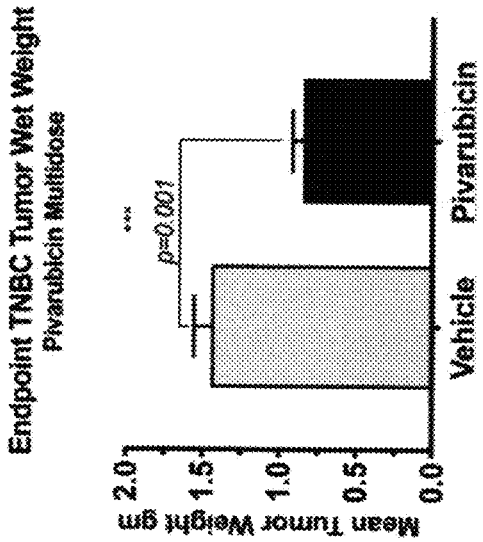
Figure 8D:
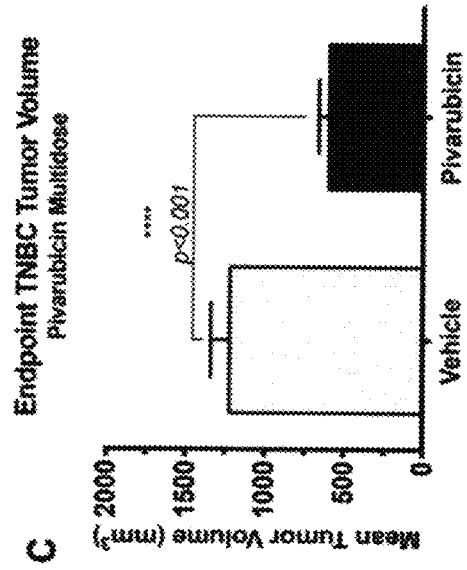

In contrast to the results for DOX, a single MTD dose of pivarubicin produced a mean 40% decrease in tumor volume compared with the mean volume prior to drug administration, indicating not only inhibition of further tumor growth but also regression of tumor mass. This is compared with a 3.5-fold increase in tumor volume in mice treated with vehicle alone (FIG. 8A). As opposed to non-tumor-bearing NSG mice, a single MTD of pivarubicin in tumor-bearing NSG mice resulted in a poorly reversible 20% mean weight loss, precluding additional dosing. As a consequence, we performed a second, independent dosing experiment in which tumor bearing NSG mice were treated with pivarubicin in two doses of 16.5 mg/kg i.p. at a two-week interval (FIG. 8B), after which the primary tumors were removed, then measured for volume (FIG. 8C) and weight (FIG. 8D). Endpoint measurements indicated that two rounds of 16.5 mg/kg pivarubicin produced a 50% decrease in tumor volume and 40% decrease in tumor weight compared with vehicle treatment.

Taken together, these results indicate that while the MTD of doxorubicin is sub-therapeutic against a rapidly growing and aggressive human TNBC orthotopic xenograft, pivarubicin not only inhibited tumor proliferation, but produced tumor regression.

Given the limitation of doxorubicin in the treatment of tumors due to irreversible cardiotoxicity due to the total cumulative dose of drug, it was next determined whether pivarubicin produced evidence of cardiotoxic damage at the total dose of drug administered to NSG mice that produced tumor growth inhibition. Histological evidence of ventricular damage in hearts of drug- or vehicle-treated NSG mice were assessed using the Bertazzoli Test, originally designed to assess doxorubicin-induced cardiomyocyte damage [29]. Analyses were performed on hearts from two independent experiments: 1) hearts that were excised at dosing endpoint from tumor-bearing NSG mice receiving 2 i.p. doses of pivarubicin at 16.5 mg/kg, doxorubicin at 1.4 mg/kg then 1.6 mg/kg and an equivalent volume of vehicle alone and 2) non-tumor-bearing female NSG mice receiving 3 i.p. doses of pivarubicin at 16.5 mg/kg, doxorubicin at 1.4 mg/kg then 1.6 mg/kg×2 and an equivalent volume of vehicle alone at 2-week intervals.

As shown in Table 4, non-tumor-bearing mice (n=9) that were given a cumulative dose of pivarubicin that was demonstrated to inhibit primary TNBC tumor growth exhibited no evidence of histologic damage to ventricular cardiomyocytes, as measured by both severity of damage to individual cells and extent of the lesion. Similarly, 9/10 hearts from tumor bearing NSG mice treated with pivarubicin at a cumulative tumor growth inhibitory dose showed no evidence of myocardial damage. In contrast, doxorubicin treatment of non-tumor-bearing mice at its sub-therapeutic MTD resulted in detectable damage to cardiomyocytes in 4/9 hearts, based on severity. DOX-treated tumor-bearing mice exhibited less cardiotoxicity (2/9 hearts) but received a lower cumulative dose than non-tumor-bearing mice. Paradoxically, vehicle-treated mice from both experiments (tumor-bearing, n=18; non-tumor-bearing, n=10) exhibited evidence of myocardial damage in 4/18 and 2/9 hearts, respectively. FIGS. 9A-9C shows representative stained thin-sections of the ventricular cardiomyocytes from non-tumor-bearing mouse hearts showing visible evidence of microvacuolization. These results gave evidence that at a cumulative dose that inhibits TNBC tumor growth, pivarubicin produced no detectable cardiac damage.

TABLE 4

Cardiotoxicity analysis of non-tumor-bearing and TNBC-bearing NSG mice.

| | Non-Tumor-Bearing | | | Tumor-Bearing | | |
|---|---|---|---|---|---|---|
| | Vehicle | DOX | PIV | Vehicle | DOX | PIV |
| Severity | | | | | | |
| 0 | 7/9 | 5/9 | 9/9 | 13/18 | 7/9 | 9/10 |
| 0.5 | 0/9 | 0/9 | 0/9 | 0/18 | 0/9 | 0/10 |
| 1.0 | 2/9 | 4/9 | 0/9 | 5/18 | 2/9 | 1/10 |
| Total Score | | | | | | |
| 0 | 7/9 | 7/9 | 9/9 | 14/18 | 8/9 | 9/10 |
| 0.5 | 2/9 | 2/9 | 0/9 | 4/18 | 1/9 | 0/10 |
| 1.0 | 0/9 | 0/9 | 0/9 | 0/18 | 0/9 | 1/10 |

The data for Table 4 was generated as follows. Non-tumor-bearing female NSG mice at 9 weeks old were treated with either 16.5 mg/kg pivarubicin (PIV), 1.4 mg/kg (1×) and 1.6 mg/kg (2×) doxorubicin and equivalent volumes of vehicle i.p. at 2-week intervals. Tumor-bearing female NSG mouse treatment was as described for the "Cardiotoxicity Assessment method" method. At endpoint, hearts were excised and prepared for histological analysis as described above. Severity and severity×extension (total score) are defined in Materials and Methods.

Declarations

Ethics Approval for Studies Involving Animals: All animal studies were approved by The University of Tennessee Health Science Center IACUC.

Availability of Data and Materials: The datasets used and/or analyzed during the current study are available from the corresponding author on reasonable request.

REFERENCES

1. O'Reilly E A, Gubbins L, Sharma S, Tully R, Guang M H, Weiner-Gorzel K, McCaffrey J, Harrison M, Furlong F, Kell M, McCann A: The fate of chemoresistance in triple negative breast cancer (TNBC). BBA Clin 2015, 3:257-275.
2. Omarini C, Guaitoli G, Pipitone S, Moscetti L, Cortesi L, Cascinu S, Piacentini F: Neoadjuvant treatments in triple-negative breast cancer patients: where we are now and where we are going. Cancer Manag Res 2018, 10:91-103.
3. Sharma P: Update on the Treatment of Early-Stage Triple-Negative Breast Cancer. Curr Treat Options Oncol. 2018, 19:22.
4. Jhan J R, Andrechek E R: Triple-negative breast cancer and the potential for targeted therapy. Pharmacogenomics. 2017, 18:1595-1609.
5. Liedtke C, Mazouni C, Hess, K R, Andre', F, Tordai A, Mejia J A, Symmans W F, Gonzalez-Angulo A M, Hennessy B, Green M, Cristofanilli M, Hortobagyi G N, Pusztai L: Response to neoadjuvant therapy and long-term survival in patients with triple-negative breast cancer. J Clin Oncol 2008, 26:1275-1281.
6. Amos K D, Adamo B, Anders C K: Triple-negative breast cancer: an update on neoadjuvant clinical trials. Int J Breast Cancer 2012, 2012:385978.
7. Yeh E T, Bickford C L: Cardiovascular complications of cancer therapy: incidence, pathogenesis, diagnosis, and management. J Am Coll Cardiol 2009, 53:2231-2247.
8. Menna P, Salvatorelli E, Minotti G: Cardiotoxicity of antitumor drugs. Chem Res Toxicol 2008, 21:978-989.
9. Lothstein L, Israel M, Sweatman T W: Anthracycline drug targeting: cytoplasmic versus nuclear—a fork in the road. Drug Resist Update 2001, 4:169-177.
10. Roaten J B, Kazanietz M G, Caloca M J, Bertics P J, Lothstein L, Parrill A L, Israel M, Sweatman T W: Interaction of the novel anthracycline antitumor agent N-benzyladriamycin-14-valerate with the C1-regulatory domain of protein kinase C: structural requirements, isoform specificity, and correlation with drug cytotoxicity. Mol Cancer Ther 2002, 1:483-492.
11. Roaten J B, Kazanietz M G, Sweatman T W, Lothstein L, Israel M, Parrill A L: Molecular models of N-benzyladriamycin-14-valerate (AD 198) in complex with the phorbol ester-binding C1b domain of protein kinase C-delta. J Med Chem 2001, 44:1028-1034.
12. Barrett C M, Lewis F L, Roaten J B, Sweatman T W, Israel M, Cleveland J L, Lothstein L: Novel extranuclear-targeted anthracyclines override the antiapoptotic functions of Bcl-2 and target protein kinase C pathways to induce apoptosis. Mol Cancer Ther 2002, 1:469-481.
13. Lothstein L, Savranskaya L, Barrett C M, Israel M, Sweatman T W: N-Benzyladriamycin-14-valerate (AD 198) activates protein kinase C-delta holoenzyme to trigger mitochondrial depolarization and cytochrome c release independently of permeability transition pore opening and Ca2+ influx. Anticancer Drugs 2006, 17:495-502.
14. Lothstein L, Savranskaya L, Sweatman T W: N-Benzyladriamycin-14-valerate (AD 198) cytotoxicity circumvents Bcr-Abl anti-apoptotic signaling in human leukemia cells and also potentiates imatinib cytotoxicity. Leuk Res 2007, 31:1085-1095.
15. He Y, Liu J, Durrant D, Yang H S, Sweatman T, Lothstein L, Lee R M: N-benzyladriamycin-14-valerate (AD 198) induces apoptosis through protein kinase C-delta-induced phosphorylation of phospholipid scramblase 3. Cancer Res 2005, 65:10016-10023.
16. He Y, Liu J, Grossman D, Durrant D, Sweatman T, Lothstein L, Epand R F, Epand R M, Lee R M: Phosphorylation of mitochondrial phospholipid scramblase 3 by protein kinase C-delta induces its activation and facilitates mitochondrial targeting of tBid. J Cell Biochem 2007, 101:1210-1221.
17. Hofmann P A, Israel M, Koseki Y, Laskin J, Gray J, Janik A, Sweatman T W, Lothstein L: N-Benzyladriamycin-14-valerate (AD 198): a non-cardiotoxic anthracycline that is cardioprotective through PKC-epsilon activation. J Pharmacol Exp Ther 2007, 323:658-664.
18. Cai C, Lothstein L, Morrison R R, Hofmann P A: Protection from doxorubicin-induced cardiomyopathy using the modified anthracycline N-benzyladriamycin-14-valerate (AD 198). J Pharmacol Exp Ther 2010, 335:223-230.
19. Lothstein L, Suttle D P, Roaten J B, Koseki Y, Israel M, Sweatman T W: Catalytic inhibition of DNA topoisomerase II by N-benzyladriamycin (AD 288). Biochem Pharmacol 2000, 60:1621-1628.
20. Lothstein L, Rodrigues P J, Sweatman T W, Israel M: Cytotoxicity and intracellular biotransformation of N-benzyladriamycin-14-valerate (AD 198) are modulated by changes in 14-O-acyl chain length. Anticancer Drugs 1998, 9:58-66.
21. Israel M, Idriss J M, Koseki Y, Khetarpal V K: Comparative effects of adriamycin and DNA-non-binding analogues on DNA, RNA, and protein synthesis in vitro. Cancer Chemother Pharmacol 1987, 20:277-284.
22. Beck W T, Mueller T J, Tanzer L R: Altered surface membrane glycoproteins in Vinca alkaloid-resistant human leukemic lymphoblasts. Cancer Res 1979, 39:2070-2076.
23. Conter V, Beck W T: Acquisition of multiple drug resistance by CCRF-CEM cells selected for different degrees of resistance to vincristine. Cancer Treat Rep 1984, 68:831-839.
24. Lu X, Yan C H, Yuan M, Wei Y, Hu G, Kang Y: In vivo dynamics and distinct functions of hypoxia in primary tumor growth and organotropic metastasis of breast cancer. Cancer Res 2010 70:3905-3914.
25. Yoshida K, Wang H G, Miki Y, Kufe D: Protein kinase Cdelta is responsible for constitutive and DNA damage-induced phosphorylation of Rad9. EMBO J 2003, 22:1431-1441.
26. Sweatman T W, Seshadri R, Israel M: Pharmacology of N-benzyladriamycin-14-valerate in the rat. Cancer Chemother Pharmacol 1999, 43:419-426.
27. Sweatman T W, Israel M: Comparative metabolism and elimination of adriamycin and 4'-epiadriamycin in the rat. Cancer Chemother Pharmacol 1987, 19:201-206.
28. Mosmann T: Rapid colorimetric assay for cellular growth and survival: application to proliferation and cytotoxicity assays. J Immunol Methods 1983, 65:55-63.
29. Bertazzoli C, Bellini O, Magrini U, Tosana M G: Quantitative experimental evaluation of adriamycin cardiotoxicity in the mouse. Cancer Treat Rep 1979, 63:1877-1883.
30. Holliday D L, Speirs V: Choosing the right cell line for breast cancer research. Breast Cancer Res 2011, 13: 215.
31. Zeichner S B, Terawaki H, Gogineni K: A review of systemic treatment in metastatic triple-negative breast cancer. Breast Cancer (Auckl) 2016, 10:25-36.
32. Sweatman T W, Parker R F, Israel M: Pharmacologic rationale for intravesical N-trifluoroacetyladriamycin-14-valerate (AD 32): a preclinical study. Cancer Chemother Pharmacol 1991, 28:1-6.
33. Hauge E, Christiansen H, Rosada C, de Darkó E, Dam T N, Stenderup K: Topical valrubicin application reduces skin inflammation in murine models. Br J Dermatol 2012, 167:288-295.
34. Rottboell L, de Foenss S, Thomsen K, Christiansen H, Andersen S M, Dam T N, Rosada C, Stenderup K. Exploring valrubicin's effect on *Propionibacterium acnes*-induced skin inflammation in vitro and in vivo. Dermatol Reports 2015, 7:6246.
35. Johnson R, Sabnis N, Sun X, Ahluwalia R, Lacko A G: SR-B1-targeted nanodelivery of anti-cancer agents: a promising new approach to treat triple-negative breast cancer. Breast Cancer 2017, 9:383-392.
36. Rathore K, Cekanova M: A novel derivative of doxorubicin, AD198, inhibits canine transitional cell carcinoma and osteosarcoma cells in vitro. Drug Des Devel Ther 2015, 9:5323-5335.
37. Pawlik C A, Israel M, Sweatman T W, Lothstein L: Cellular resistance against the novel hybrid anthracycline N-(2-chloroethyl)-N-nitrosoureidodaunorubicin (AD 312) is mediated by combined altered topoisomerase II and O6-methylguanine-DNA methyltransferase activities. Oncol Res 1998; 10:209-217.
38. Ganapathi R, Grabowski D, Sweatman T W, Seshadri R, Israel M: N-Benzyladriamycin-14-valerate versus progressively doxorubicin-resistant murine tumours: cellular pharmacology and characterisation of cross-resistance in vitro and in vivo. Br J Cancer 1989, 60:819-826.
39. Huang W C, Su H H, Fang L W, Wu S J, Liou C J: Licochalcone A inhibits cellular motility by suppressing E-cadherin and MAPK signaling in breast cancer. Cells 2019, 8: E218.
40. Hwang E, Hwang S H, Kim J, Park J H, Oh S, Kim Y A, Hwang K T: ABT-737 ameliorates docetaxel resistance in triple negative breast cancer cell line. Ann Surg Treat Res 2018, 95:240-248.
41. Inao T, Iida Y, Moritani T, Okimoto T, Tanino R, Kotani H, Harada M. Bcl-2 inhibition sensitizes triple-negative human breast cancer cells to doxorubicin. Oncotarget 2018, 9:25545-25556.
42. Lovitt C J, Shelper T B, Avery V M: Doxorubicin resistance in breast cancer cells is mediated by extracellular matrix proteins. BMC Cancer 2018, 18:41.
43. Campbell K J, Tait S W G. Targeting BCL-2 regulated apoptosis in cancer. Open Biol. 2018, 8:180002.
44. Balko J M, Giltnane J M, Wang K, Schwarz L J, Young C D, Cook R S, Owens P, Sanders M E, Kuba M G, Sanchez V, Kurupi R, Moore P D, Pinto J A, Doimi F D, Gómez H, Horiuchi D, Goga A, Lehmann B D, Bauer J A, Pietenpol J A, Ross J S, Palmer G A, Yelensky R, Cronin M, Miller V A, Stephens P J, Arteaga C L. Molecular profiling of the residual disease of triple-negative breast cancers after neoadjuvant chemotherapy identifies actionable therapeutic targets. Cancer Discov 2014, 4:232-245.
45. Lee K M, Giltnane J M, Balko J M, Schwarz L J, Guerrero-Zotano A L, Hutchinson K E, Nixon M J, Estrada M V, Sánchez V, Sanders M E, Lee T, Gómez H, Lluch A, Pérez-Fidalgo J A, Wolf M M, Andrejeva G, Rathmell, J C, Fesik S W, Arteaga C L. MYC and MCL1 Cooperatively Promote Chemotherapy-Resistant Breast Cancer Stem Cells via Regulation of Mitochondrial Oxidative Phosphorylation. Cell Metab 2017, 26:633-647.
46. Edwards S K, Moore C R, Liu Y, Grewal S, Covey L R, Xie P. N-Benzyladriamycin-14-valerate (AD 198) exhibits potent anti-tumor activity on TRAF3-deficient mouse B lymphoma and human multiple myeloma. BMC Cancer 2013, 13:481.
47. Pandey S, Bourn J, Cekanova M: Mutations of p53 decrease sensitivity to the anthracycline treatments in bladder cancer cells. Oncotarget 2018, 9:28514-28531
48. Pommier Y, Leo E, Zhang H, Marchand C: DNA topoisomerases and their poisoning by anticancer and antibacterial drugs. Chem Biol 2010, 17:421-433.
49. Wang C, Zhang J, Wang Y, Ouyang T, Li J, Wang T, Fan Z, Fan T, Lin B, Xie Y: Prevalence of BRCA1 mutations and responses to neoadjuvant chemotherapy among BRCA1 carriers and non-carriers with triple-negative breast cancer. Ann Oncol 2015, 26:523-528.
50. O'Connor P M, Jackman J, Bae I, Myers T G, Fan S, Mutoh M, Scudiero D A, Monks A, Sausville E A, Weinstein J N, Friend S, Fornace A J Jr, Kohn K W: Characterization of the p53 tumor suppressor pathway in cell lines of the National Cancer Institute anticancer drug screen and correlations with the growth-inhibitory potency of 123 anticancer agents. Cancer Res 1997, 57:4285-4300.
51. Bilyeu J D, Panta G R, Cavin L G, Barrett C M, Turner E J, Sweatman T W, Israel M, Lothstein L, Arsura M: Circumvention of nuclear factor kappaB-induced chemoresistance by cytoplasmic-targeted anthracyclines. Mol Pharmacol 2004, 65:1038-1047.
52. Zhang L H, Yang A J, Wang M, Liu W, Wang C Y, Xie X F, Chen X, Dong J F, Li M. Enhanced autophagy reveals vulnerability of P-gp mediated epirubicin resistance in triple negative breast cancer cells. Apoptosis 2016, 21:473-488.
53. Boichuk S, Galembikova A, Sitenkov A, Khusnutdinov R, Dunaev P, Valeeva E, Usolova N: Establishment and characterization of a triple negative basal-like breast cancer cell line with multi-drug resistance. Oncol Lett 2017, 14:5039-5045.
54. Chung F S, Santiago J S, Jesus M F, Trinidad C V, See M F. Disrupting P-glycoprotein function in clinical settings: what can we learn from the fundamental aspects of this transporter? Am J Cancer Res 2016, 6:1583-1598.
55. Zhang Y K, Wang Y J, Gupta P, Chen Z S: Multidrug resistance proteins (MRPs) and cancer therapy. AAPS J. 2015, 17:802-812.
56. Kopecka J, Rankin G M, Salaroglio I C, Poulsen S A, Riganti C: P-glycoprotein mediated chemoresistance is reversed by carbonic anhydrase XII inhibitors. Oncotarget 2016, 7:85861-85875.
57. McCracken M A, Miraglia L J, McKay R A, Strobl J S: Protein kinase C delta is a prosurvival factor in human breast tumor cell lines. Mol Cancer Ther 2003, 2:273-281.
58. Chauvin L, Goupille C, Blanc C, Pinault M, Domingo I, Guimaraes C, Bougnoux P, Chevalier S, Mahéo K: Long chain n-3 polyunsaturated fatty acids increase the efficacy of docetaxel in mammary cancer cells by downregulating Akt and PKCε/δ-induced ERK pathways. Biochim Biophys Acta 2016, 1861:380-390.
59. Zuo Y, Wu Y, Chakraborty C: Cdc42 negatively regulates intrinsic migration of highly aggressive breast cancer cells. J Cell Physiol 2012, 227:1399-1407.
60. Chen P, Lu N, Ling Y, Chen Y, Hui H, Lu Z, Song X, Li Z, You Q, Guo Q: Inhibitory effects of wogonin on the invasion of human breast carcinoma cells by downregulating the expression and activity of matrix metalloproteinase-9. Toxicology 2011, 282:122-128.
61. Shanmugam M, Krett N L, Maizels E T, Murad F M, Rosen S T, Hunzicker-Dunn M: A role for protein kinase C delta in the differential sensitivity of MCF-7 and MDA-MB 231 human breast cancer cells to phorbol ester-induced growth arrest and p21(WAFI/CIP1) induction. Cancer Lett 2001, 172:43-53.
62. Vucenik I, Ramakrishna G, Tantivejkul K, Anderson L M, Ramljak D: Inositol hexaphosphate (IP6) blocks proliferation of human breast cancer cells through a PKCdelta-dependent increase in p27Kip1 and decrease in retinoblastoma protein (pRb) phosphorylation. Breast Cancer Res Treat 2005, 91:35-45.
63. Bird B R, Swain S M. Cardiac toxicity in breast cancer survivors: review of potential cardiac problems. Clin Cancer Res 2008, 14:14-24.
64. Babiker H M, McBride A, Newton M, Boehmer L M, Drucker A G, Gowan M, Cassagnol M, Camenisch T D, Anwer F, Hollands J M: Cardiotoxic effects of chemotherapy: A review of both cytotoxic and molecular targeted oncology therapies and their effect on the cardiovascular system. Crit Rev Oncol Hematol 2018, 126:186-200.
65. Lien M Y, Liu L C, Wang H C, Yeh M H, Chen C J, Yeh S P, Bai L Y, Liao Y M, Lin C Y, Hsieh C Y, Lin C C, Li L Y, Lin P H, Chiu C F: Safety and efficacy of pegylated liposomal doxorubicin-based adjuvant chemotherapy in patients with stage I-III triple-negative breast cancer. Anticancer Res 2014, 34:7319-7326.
66. Renu K, V G A, P B T P, Arunachalam S. Molecular mechanism of doxorubicin-induced cardiomyopathy—An update. Eur J Pharmacol 2018, 818:241-253.
67. Nitiss K C, Nitiss J L: Twisting and ironing: doxorubicin cardiotoxicity by mitochondrial DNA damage. Clin Cancer Res 2014, 20:4737-4739.
68. Zhang S, Liu X, Bawa-Khalfe T, Lu L S, Lyu Y L, Liu L F, Yeh E T: Identification of the molecular basis of doxorubicin-induced cardiotoxicity. Nat Med 2012, 18:1639-1642.
69. Sanchez H, Zoll J, Bigard X, Veksler V, Mettauer B, Lampert E, Lonsdorfer J, Ventura-Clapier R. Effect of cyclosporin A and its vehicle on cardiac and skeletal muscle mitochondria: relationship to efficacy of the respiratory chain. Br J Pharmacol 2001, 133:781-788.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

We claim:

1. A composition comprising at least one of pivarubicin and benzarubicin, or a pharmaceutically acceptable salt thereof, and further comprising a nonionic surfactant, wherein said nonionic surfactant comprises polyethyleneglycol (15)-hydroxystearate,
wherein said nonionic surfactant is present in an amount of 0.1 to 5%,
wherein said benzarubicin is present in an amount of about 0.5-3.0 mg/mL, and
wherein said pivarubicin is present in an amount of about 0.5-3.0 mg/mL.

2. The composition of claim 1, wherein said nonionic surfactant is present in an amount of about 0.125%.

3. The composition of claim 1, wherein said composition further comprises an alcohol.

4. The composition of claim 1, wherein the nonionic surfactant is present in an amount of about 0.1% to 1.0%.

5. The composition of claim 1, wherein the composition comprises pivarubicin, and wherein the composition is free of benzarubicin.

6. The composition of claim 1, wherein the pivarubicin is present in an amount of about 1 mg/mL.

7. The composition of claim 1, wherein the benzarubicin is present in an amount of about 0.75-2.5 mg/mL.

8. The composition of claim 1, wherein the benzarubicin is present in an amount of about 1 mg/mL.

9. The composition of claim 1, said composition comprising both said pivarubicin and said benzarubicin, wherein the pivarubicin is present in an amount of about 1 mg/mL, and wherein the benzarubicin is present in an amount of about 1 mg/mL.

10. The composition of claim 1, wherein said composition is formulated for parenteral administration.

* * * * *